United States Patent [19]

Buckler et al.

[11] 4,297,273

[45] Oct. 27, 1981

[54] CHEMILUMINESCENT PHTHALHYDRAZIDE-LABELED PROTEIN AND POLYPEPTIDE CONJUGATES

[75] Inventors: Robert T. Buckler, Edwardsburg, Mich.; Hartmut R. Schroeder, Elkhart, Ind.

[73] Assignee: Miles Laboratories, Inc., Elkhart, Ind.

[21] Appl. No.: 111,809

[22] Filed: Jan. 14, 1980

Related U.S. Application Data

[62] Division of Ser. No. 927,621, Jul. 24, 1978.

[51] Int. Cl.³ .................................................. C07G 7/00
[52] U.S. Cl. ............................. 260/112 B; 23/230 B; 260/112 R; 260/112.5 R; 260/112.7; 424/8; 424/12; 424/85; 424/88; 424/177; 435/7; 435/188; 525/420
[58] Field of Search ............ 260/112 R, 112 B, 112.7; 424/85, 88, 177, 12; 435/7; 435/188

[56] References Cited

U.S. PATENT DOCUMENTS

| 4,104,029 | 8/1978 | Maier, Jr. ......................... 424/12 X |
| 4,181,650 | 1/1980 | Maier, Jr. ..................... 260/112 R X |
| 4,213,894 | 7/1980 | Buckler ........................... 424/177 X |
| 4,225,485 | 9/1980 | Buckler et al. .................. 260/112 B |

OTHER PUBLICATIONS

Analytical Chem., vol. 48, No. 13, Nov. 1976, pp. 1933–1937, Schroeder et al.
J. of Immunological Methods 21: 179–184, (1978), Pratt et al.

*Primary Examiner*—Howard E. Schain
*Attorney, Agent, or Firm*—Andrew L. Klawitter

[57] ABSTRACT

Chemiluminescent-labeled conjugates of the formula:

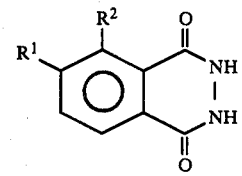

wherein one of $R^1$ and $R^2$ is hydrogen and the other is $-NR^3R^4$; $R^3$ is hydrogen or straight chain alkyl containing 1–4 carbon atoms and $R^4$ is $$L(CO)-HN-(CH_2)_n$$

wherein $n = 2-8$ and $L(CO)-$ is an antigenic protein or polypeptide bound through an amide bond. The labeled conjugates are useful as reagents in specific binding assays for determining antigenic proteins or polypeptides, or their binding partners, in liquid media.

10 Claims, No Drawings

CHEMILUMINESCENT PHTHALHYDRAZIDE-LABELED PROTEIN AND POLYPEPTIDE CONJUGATES

This is a division of application Ser. No. 927,621, filed July 24, 1978.

BACKGROUND OF THE INVENTION

1. Field of the Invention

This invention relates to novel chemiluminescent-labeled conjugates for use in specific binding assays for a ligand, such as an antigen, hapten or antibody, in a liquid medium such as a body fluid. The invention further relates to intermediate compounds produced in the synthesis of the novel labeled conjugates.

2. Brief Description of the Prior Art

Specific binding assay methods have undergone a technological evolution from the original competitive binding radioimmunoassay (RIA) in which a radioisotope-labeled antigen is made to compete with antigen from a test sample for binding to specific antibody. In the RIA technique, sample antigen is quantitated by measuring the proportion of radioactivity which becomes associated with the antibody by binding of the radiolabeled antigen (the bound-species of the labeled antigen) to the radioactivity that remains unassociated from antibody (the free-species) and then comparing that proportion to a standard curve. A comprehensive review of the RIA technique is provided by Skelly et al, Clin. Chem. 19:146(1973). While by definition RIA is based on the binding of specific antibody with an antigen or hapten, radiolabeled binding assays have been developed based on other specific binding interactions, such as between hormones and their binding proteins.

From the radiolabeled binding assays have evolved nonradioisotopic binding assays employing labeling substances such as enzymes as described in U.S. Pat. Nos. 3,654,090 and 3,817,837. Recently further improved nonradioisotopic binding assays have been developed as described in German Offenlegungschriften Nos. 2,618,419 and 2,618,511 based on U.S. Ser. Nos. 667,982 and 667,996, filed on Mar. 18, 1976 now abandoned and assigned to the present assignee, employing particularly unique labeling substances, including coenzymes, cyclic reactants, cleavable fluorescent enzyme substrates, and chemiluminescent molecules. The chemiluminescent labels consist of an organic molecule which undergoes a change in chemical structure with the production of light.

Specific examples of substances useful as chemiluminescent labels mentioned in German OLS No. 2,618,511 are luminol, isoluminol, pyrogallol and luciferin. In particular, an example is provided in the OLS [and in Anal. Chem. 48:1933(1976) based on the same work] of an isoluminol-labeled conjugate wherein isoluminol is coupled through its amino function by a 2-hydroxypropylene bridge to the ligand biotin. The isoluminol-labeled conjugate is monitored in the binding assay by measuring the production of light in the presence of either hydrogen peroxide and peroxidase or potassium superoxide. The chemiluminescent phthalhydrazide-labeled conjugates wherein an amino-phthalhydrazide is coupled through its amino function by a 2-hydroxyalkylene bridge to a ligand are described in pending U.S. patent application Ser. No. 927,622, filed on July 24, 1978 and assigned to the present assignee.

SUMMARY OF THE INVENTION

The efficiency of the amino-phthalhydrazides as chemiluminescent labels has now been improved by coupling through the amino function with an unsaturated straight chain alkylene bridge. The labeled conjugates of the present invention have the formula

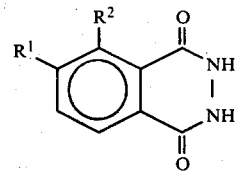

wherein one of $R^1$ and $R^2$, preferably $R^2$, is hydrogen and the other is $-NR^3R^4$; $R^3$ is hydrogen or straight chain alkyl containing 1–4 carbon atoms, preferably ethyl, and $R^4$ is $$L(CO)-HN-(CH_2)_n$$

wherein $n = 2-8$, preferably 4 or 6, and $L(CO)-$ is a specifically bindable ligand, or a binding analog thereof, bound through an amide bond.

The subject chemiluminescent phthalhydrazide-labeled conjugates are used in specific binding assays for detecting the ligand or a binding partner thereof. The labeled conjugates are monitored in the performance of a binding assay by oxidizing the labeled conjugates and measuring the light produced either as total light produced or peak light intensity. For instance, a specific binding assay for determining a hapten in a liquid medium might be carried out by incubating a sample of the liquid medium with an antibody for such hapten and with a labeled conjugate of the present invention wherein such hapten or a binding analog is labeled with the subject chemiluminescent moiety. During the incubation, any hapten present in the liquid medium competes with the labeled conjugate for binding with the antibody. Thereafter, the amount of labeled conjugate resulting in the bound-species compared to the free-species (which amount is an inverse function of the amount of hapten in the liquid medium assayed) is determined (i.e., monitored) either in a homogeneous fashion, if the chemiluminescent character of the labeled conjugate is different when in the bound-species than when in the free-species, or in a heterogeneous fashion, if such character is essentially the same in both species. In the homogeneous assay, the unseparated reaction mixture containing both species of the labeled conjugate is combined with an appropriate oxidation system for the chemiluminescent label and the light produced is measured. In the heterogeneous assay, the bound- and free-species are separated by any conventional technique, the oxidation system combined with one thereof, and the light produced is measured.

The monitorable chemiluminescent reaction may be illustrated as follows:

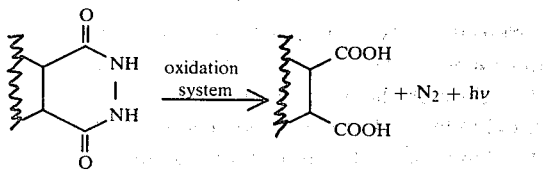

wherein hν represents electromagnetic radiation emitted. Useful oxidation systems include hydrogen peroxide combined with any of the following catalysts, peroxidase (particularly microperoxidase), catalase, deuterohemin, hematin or ferricyanide ions; hypochlorite ions combined with cobalt ions; persulfate ions; potassium superoxide; periodate ions; hypoxxanthine combined with xanthine oxidase; or potassium t-butoxide.

The chemiluminescent-labeled conjugates may be employed in any conventional homogeneous or heterogeneous binding assay method, including competitive binding methods, sequential saturation methods, direct binding methods, and "sandwich" binding method. Further details concerning the state of the art for binding assay techniques may be found in the aforementioned German OLS Nos. 2,618,419 and 2,618,511.

In the context of this disclosure, the following terms shall be defined as follows unless otherwise indicated: "specifically bindable ligand" is an organic substance of analytical interest for which there is a specific binding partner, "specific binding partner of the ligand" is the substance which has a noncovalent binding affinity for the ligand to the exclusion of other substances; and "binding analog of the ligand" is an organic substance which is different in chemical structure from the ligand but which behaves essentially the same as the ligand with respect to the binding affinity of the specific binding partner of the ligand.

The chemical nature of the specifically bindable ligand or analog thereof in the present labeled conjugates is usually a protein, polypeptide, peptide, carbohydrate, glycoprotein, steroid, or other organic molecule for which a specific binding partner is obtainable. In functional terms, the ligand will usualy be an antigen or an antibody thereto; a hapten or an antibody thereto; or a hormone, vitamin, or drug, or a receptor or binding substance therefor. Most commonly, the ligand is an immunologically-active polypeptide or protein of molecular weight between 1,000 and 4,000,000 such as an antigenic polypeptide or protein or an antibody; or is a hapten of molecular weight between 100 and 1,500.

The present labeled conjugates are prepared usually by forming a peptide or amide couple between (1) an amino derivative of a chemiluminescent aminophthal-hydrazide (e.g., luminol or isoluminol) and (2) either the ligand, where such contains a carboxylic acid function, or a binding analog of the ligand (e.g., a derivative of the ligand) which analog contains the desired carboxylic acid function. Such condensation reactions can be accomplished by reacting the amino derivative of the label directly with the carboxylic acid-containing ligand or ligand analog using conventional peptide condensation reactions such as the carbodiimide reaction [Science 144:1344 (1974)], the mixed anhydride reaction [Erlanger, et al, Methods in Immunology and Immunochemistry, ed. Williams and Chase, Academic Press (New York 1967) p. 149], and the acid azide and active ester reactions [Kopple, Peptides and Amino Acids, W. A. Benjamin, Inc. (New York 1966)]. See also for a general review Clin. Chem. 22:726(1976).

It will be recognized of course that other well known methods are available for coupling the ligand or a derivative thereof to the amino-derivative of the label. In particular, conventional bifunctional coupling agents may be employed for coupling a ligand, or its derivative, containing a carboxylic acid or amino group to the amino-derivative of the label. For example, amine-amine coupling agents such as bis-isocyanates, bis-imidoesters, and glutaraldehyde [Immunochem. 6:53(1969)] may be used to couple a ligand or derivative containing an amino group to the amino-derivative of the label. Also, appropriate coupling reactions are well known for inserting a bridge group in coupling an amine (e.g., the amino-derivative of the label) to a carboxylic acid (e.g., the ligand or a derivative thereof). Coupling reactions of this type are thoroughly discussed in the literature, for instance in the above-mentioned Kopple monograph and in Lowe & Dean, Affinity Chromatography, John Wiley & Sons (New York 1974).

Such coupling techniques will be considered equivalents to the previously discussed peptide condensation reactions in preparing useful labeled conjugates. The choice of coupling technique will depend on the functionalities available in the ligand or analog thereof for coupling to the label derivative and on the length of bridging group desired. In all cases, for the purpose of this disclosure, the resulting labeled conjugate will comprise the label derivative bound to the remaining portion of the conjugate through an amide bond. Such remaining portion of the conjugate will be considered as a residue of a binding analog of the ligand, unless the ligand itself is directly coupled to the label derivative. Thus, in this description and in the claims to follow, the abbreviation L(CO-)- represents the ligand or a binding analog thereof coupled through an amide bond, wherein such analog may be a derivative of the ligand coupled by peptide condensation to the label derivative or may be the ligand or derivative thereof coupled through a bridging group inserted by coupling of the ligand or derivative to the label derivative with a bifunctional coupling agent.

Preparation of the present chemiluminescent-labeled conjugates proceeds according to the following general synthetic sequence:

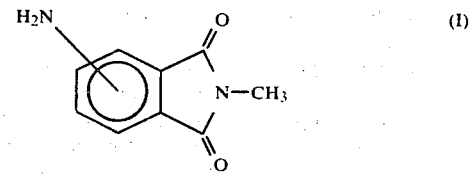

The starting material for the synthesis is 3- or 4-amino-N-methylphthalimide (I) with the 3-amino compound [Wang et al, JACS 72:4887(1950) and Flitsch, Chem. Ber. 94:2494(1961)] to be used to prepare luminol based labeled-conjugates and the 4-amino compound [Flitsch, Chem. Ber. 94:2494(1961)] to be used to prepare isoluminol based labeled-conjugates.

Reaction of the phthalimide (I) with an N-(ω-bromoalkyl) phthalimide (II) [available from Aldrich Chemical Co., Milwaukee, Wisconsin U.S.A., or see Derscherl and Weingarten, Justus Liebig's Annalen der Chemie 574:131(1951)]

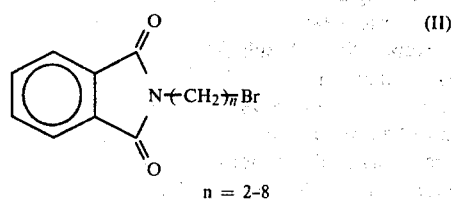

(II)

n = 2-8 produces the bis-phthalimide intermediate (III).

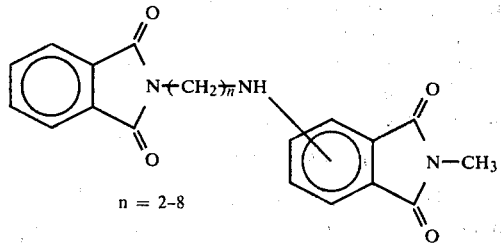

(III)

n = 2-8

Alkylation of the amine group in the bis-phthalimide intermediate (III) is obtained by reaction with a dialkyl sulfate (IV) [Rodd, Chemistry of Carbon Compounds, vol. 1, Elsevier Publ. Co. (New York 1951) p. 337].

$$[CH_3{+}CH_2{\rightarrow}_m O]_2 SO_2 \quad \text{(IV)}$$

m = 0-3 to yield the N-alkylated derivative (V)

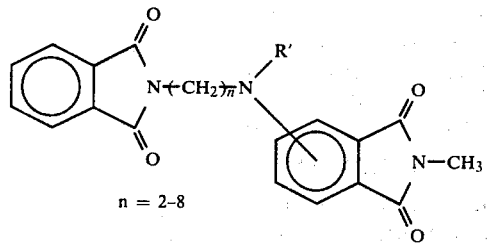

(V)

n = 2-8 wherein R' is straight chain alkyl containing 1-4 carbon atoms.

Treatment of the bis-phthalimide intermediate (III) or its N-alkylated derivative (V) with hydrazine produces the amino-hydrazide (VI)

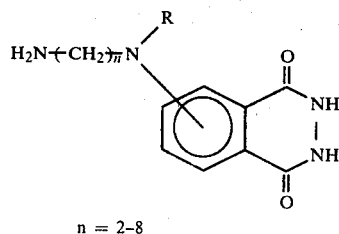

(VI)

n = 2-8 wherein R is hydrogen or straight chain alkyl containing 1-4 carbon atoms.

Condensation of the amino-hydrazide (VI) with (a) the ligand to be labeled, where such contains a carboxylic acid function, (b) a binding analog of the ligand, such analog being a carboxylic acid derivative of the ligand, or (c) the ligand or an appropriate derivative of the ligand in the presence of a bifunctional coupling agent, produces the chemiluminescent-labeled conjugate (VII)

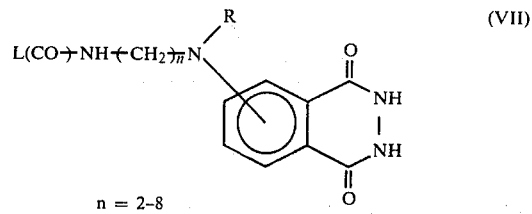

(VII)

n = 2-8 wherein R is the same as defined above and L(CO→) represents the specifically bindable ligand, or a binding analog thereof (formed by derivation of the ligand and/or insertion of a bridge by a bifunctional coupling agent), bound through an amide bond.

Other variations of labeled conjugates based on the above-described synthetic scheme are clearly evident. In particular, various ring-substituted amino-N-methylphthalimides may be used as starting material to produce ring-substituted labeled conjugates possessing substantially the same qualitative properties as the conjugates prepared according to the above-described scheme. Such conjugates will be recognized as equivalents and are exemplified by the addition of one, two or more simple substituents to an available aromatic ring site, such substituents including without limitation, alkyl, e.g., methyl, ethyl and butyl; halo, e.g., chloro and bromo; nitro; hydroxyl; alkoxy, e.g., methoxy and ethoxy, and so forth.

As illustrated in the above-described synthetic scheme, the novel intermediate compounds produced in the course of preparing the chemiluminescent-labeled conjugates have the following general formulae [the amino-hydrazides (VI) correspond to formula A below and the bis-phthalimides (III) and (V) correspond to formula B below]:

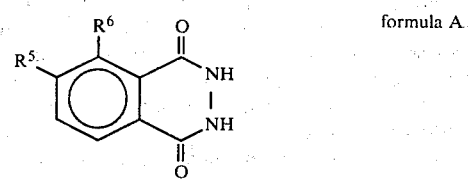

formula A wherein one of $R^5$ and $R^6$, preferably $R^6$, is hydrogen and the other is $-NR^7R^8$; $R^7$ is hydrogen or straight chain alkyl containing 1-4 carbon atoms, preferably ethyl, and $R^8$ is

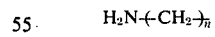

wherein n = 2-8, preferably 4 or 6; and

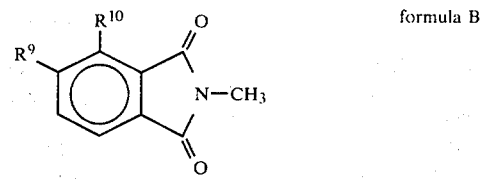

formula B wherein one of $R^9$ and $R^{10}$, preferably $R^{10}$, is hydrogen and the other is $-NR^{11}R^{12}$; $R^{11}$ is hydrogen or straight chain alkyl containing 1-4 carbon atoms, preferably ethyl, and $R^{12}$ is

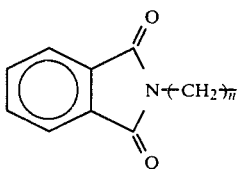

wherein n=2-8, preferably 4 or 6.

As stated hereinabove, the ligand which is comprised in the labeled conjugate or whose binding analog is comprised in the labeled conjugate is in most circumstances an immunologically-active polypeptide or protein of molecular weight between 1,000 and 4,000,000 such as an antigenic polypeptide or protein or an antibody; or is a hapten of molecular weight between 100 and 1,500. Following will now be presented various methods for coupling such ligands or analogs thereof to the amino-derivative (VI) of the label through an amide bond.

Polypeptides and Proteins

Representative of specifically bindable protein ligands are antibodies in general, particularly those of the IgG, IgE, IgM and IgA classes, for example hepatitis B antibodies; and antigenic proteins such as insulin, chorionic gonadotropin (e.g., HCG), carcinoembryonic antigen (CEA), myoglobin, hemoglobin, follicle stimulating hormone, human growth hormone, thyroid stimulating hormone (TSH), human placental lactogen, thyroxine binding globulin (TBG), instrinsic factor, transcobalamin, enzymes such as alkaline phosphatase and lactic dehydrogenase, and hepatitis-associated antigens, such as hepatitis B surface antigen ($HB_sAg$), hepatitis e antigen ($HB_eAg$) and hepatitis core antigen ($HB_cAg$). Representative of polypeptide ligands are angiotensin I and II, C-peptide, oxytocin, vasopressin, neurophysin, gastrin, secretin, and glucagon.

Since, as peptides, ligands of this general category comprise numerous available carboxylic acid and amino groups, coupling to the amino-derivative of the chemiluminescent label can proceed according to conventional peptide condensation reactions such the carbodiimide reaction, the mixed anhydride reaction, and so forth as described hereinabove, or by the use of conventional bifunctional reagents capable of coupling carboxylic acid or amino functions to the amino group in the label derivative as likewise described above. General references concerning the coupling of proteins to primary amines or carboxylic acids are mentioned in detail above.

Haptens

Haptens, as a class, offer a wide variety of organic substances which evoke an immunochemical response in a host animal only when injected in the form of an immunogen conjugate comprising the hapten coupled to a carrier molecule, almost always a protein such as albumin. The coupling reactions for forming the immunogen conjugates are well developed in the art and in general comprise the coupling of a carboxylic acid ligand or a carboxylic acid derivative of the ligand to available amino groups on the protein carrier by formation of an amide bond. Such well known coupling reactions are directly analogous to the present formation of labeled conjugates by coupling carboxylic acid ligands or binding analogs to the amino-derivative of the chemiluminescent label.

Hapten ligands which themselves contain carboxylic acid functions, and which thereby can be coupled directly to the amino-derivative of the label, include the iodothryonine hormones such as thyroxine and liothyronine, as well as other materials such as biotin, valproic acid, folic acid and certain prostaglandins. Following are representative synthetic routes for preparing carboxylic acid binding analogs of hapten ligands which themselves do not contain an available carboxylic acid function whereby such analogs can be coupled to the amino-derivative of the label by the aforementioned peptide condensation reactions or bifunctional coupling agent reactions (in the structural formulae below, n represents an integer, usually from 1 through 6).

CARBAMAZEPINE

Dibenz[b,f]azepine is treated sequentially with phosgene, an ω-aminoalkanol, and Jones reagent (chromium trioxide in sulfuric acid) according to the method of Singh, U.S. Pat. No. 4,058,511 to yield the following series of carboxylic acids:

QUINIDINE

Following the method of Cook et al, Pharmacologist 17:219(1975), quinidine is demethylated and treated with 5-bromovalerate followed by acid hydrolysis to yield a suitable carboxylic acid derivative.

DIGOXIN AND DIGITOXIN

The aglycone of the cardiac glycoside is treated with succinic anhydride and pyridine according to the method of Oliver et al, J. Clin. Invest. 47:1035(1968) to yield the following:

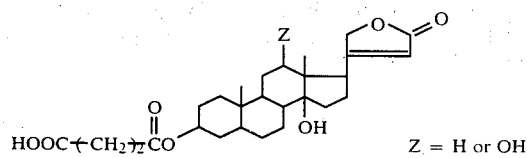

Z = H or OH

THEOPHYLLINE

Following the method of Cook et al, Res. Comm. Chem. Path. Pharm. 13:497(1976), 4,5-diamino-1,3-dimethylpyrimidine-2,6-dione is heated with glutaric anhydride to yield the following:

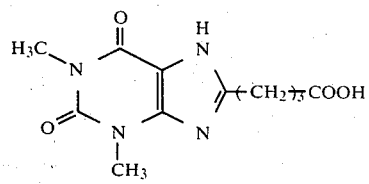

PHENOBARBITAL AND PRIMIDONE

Sodium phenobarbital is heated with methyl 5-bromovalerate and the product hydrolyzed to the corresponding acid derivative of phenobarbital [Cook et al, Quantitative Analytic Studies in Epilepsy, ed. Kelleway and Peterson, Raven Press (New York 1976) pp. 39–58]:

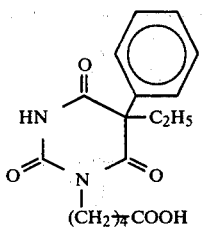

To obtain the acid derivative of primidone following the same Cook et al reference method, 2-thiophenobarbital is alkylated, hydrolyzed, and the product treated with Raney nickel to yield:

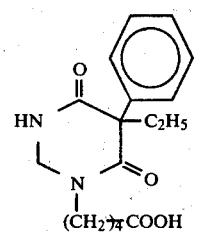

DIPHENYLHYDANTOIN

Following the method of Cook et al, Res. Comm. Chem. Path. Pharm. 5:767(1973), sodium diphenylhydantoin is reacted with methyl 5-bromovalerate followed by acid hydrolysis to yield the following:

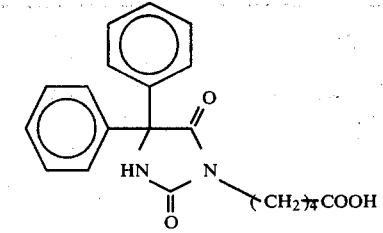

MORPHINE

Morphine free base is treated with sodium β-chloroacetate according to the method of Spector et al, Science 168:1347(1970) to yield a suitable carboxylic acid derivative.

NICOTINE

According to the method of Langone et al, Biochem. 12(24):5025(1973), trans-hydroxymethylnicotine and succinic anhydride are reacted to yield the following:

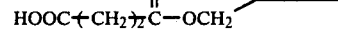

ANDROGENS

Suitable carboxylic acid derivatives of testosterone and androstenedione linked through either the 1- or 7-position on the steroid nucleus are prepared according to the method of Bauminger et al, J. Steroid Biochem. 5:739(1974). Following are representative testosterone derivatives:

1-position

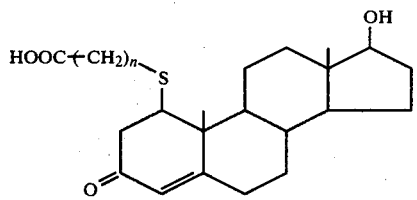

7-position

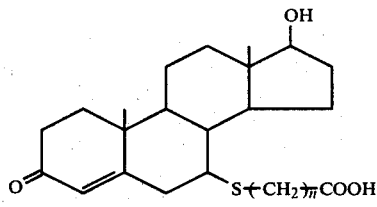

ESTROGENS

Suitable carboxylic acid derivatives of estrogens, e.g., estrone, estradiol and estriol, are prepared according to the method of Bauminger et al, supra, as represented by the following estrone derivative:

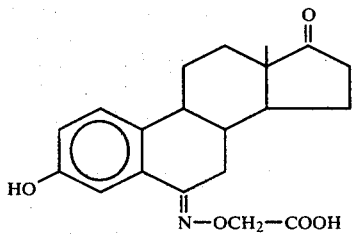

PROGESTERONES

Suitable carboxylic acid derivatives of progesterone and its metabolites linked through any of the 3-, 6- or 7-positions on the steroid nucleus are prepared according to the method of Bauminger et al, supra, as represented by the following progesterone derivatives:

3-position

-continued

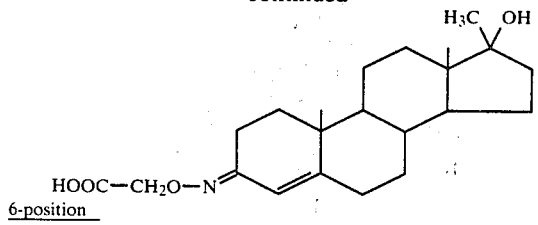
6-position

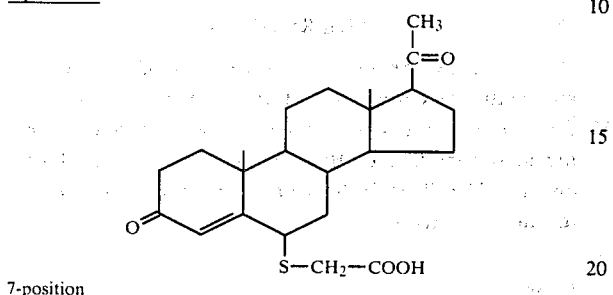
7-position

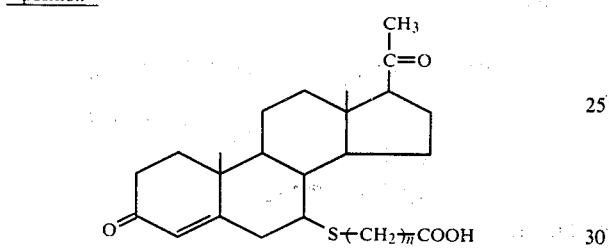

The methods described above are but examples of the many known techniques for forming suitable carboxylic acid derivatives of haptens of analytical interest. The principal derivation techniques are discussed in Clin. Chem. 22:726(1976) and include esterification of a primary alcohol with succinic anhydride [Abraham and Grover, Principles of Competitive Protein-Binding Assays, ed. Odell and Daughaday, J. B. Lippincott Co. (Philadelphia 1971) pp. 140–157], formation of an oxime from reaction of a ketone group with carboxylmethyl hydroxylamine [J. Biol. Chem. 234:1090(1959)], introduction of a carboxyl group into a phenolic residue using chloroacetate [Science 168:1347(1970)], and coupling to diazotized p-aminobenzoic acid in the manner described in J. Biol. Chem. 235:1051(1960).

The hereinbefore-described general synthetic sequence for preparing the present chemiluminescent-labeled conjugates is specifically exemplified by the following descriptions of the preparation of the labeled thyroxine conjugates 6-{N-ethyl-N-[4-(thyroxinylamido)butyl]amino}-2,3-dihydrophthalazine-1,4-dione and 6-{N-ethyl-N-[6-(thyroxinylamido)hexyl]amino}-2,3-dihydrophthalazine-1,4-dione. The reaction sequences for these syntheses are outlined in Tables 1 and 2 which follow.

A. Preparation of the Labeled Conjugates

N-Trifluoroacetylthyroxine (2).

A solution of 20 grams (g) [25.6 millimole (mmol)] of L-thyroxine (1) (Sigma Chemical Co., St. Louis, Missouri USA) in 240 milliliters (ml) of ethyl acetate containing 46 ml of trifluoroacetic acid and 7.6 ml of trifluoroacetic anhydride was stirred at 0° C. for one hour. Upon adding 200 ml of water ($H_2O$), a suspension formed that was saturated with sodium chloride. The organic phase was separated, washed with saturated aqueous sodium chloride solution, dried over anhydrous magnesium sulfate, filtered and evaporated. When dry the crystalline residue amounted to 21.3 g of the N-protected thyroxine derivative (2). A sample was recrystallized from ether-pentane to give fine white crystals, melting point (m.p.) 233°–235° C. (decomposed).

TABLE 1

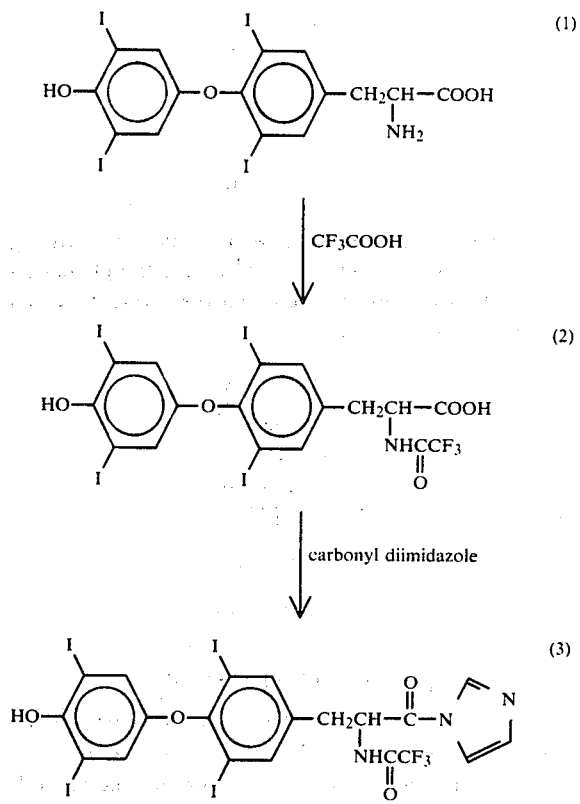

TABLE 2

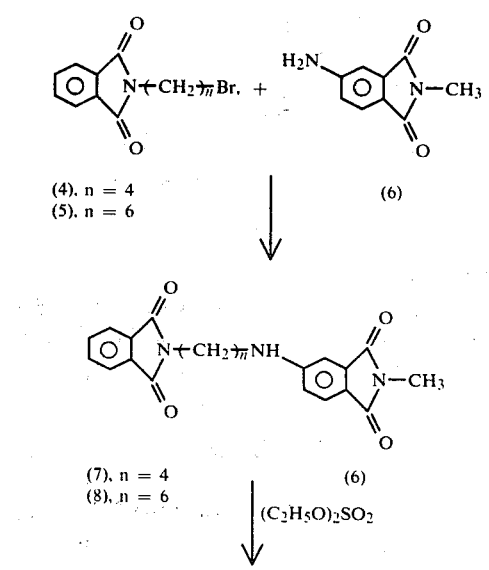

TABLE 2-continued

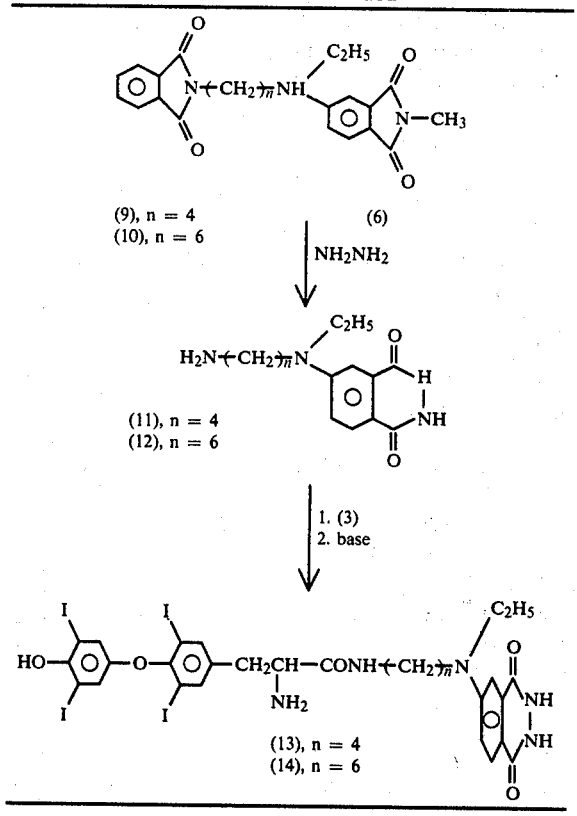

Analysis: Calculated for $C_{17}H_{10}F_3I_4NO_5$: C, 23.39; H, 1.15; N 1.60. Found: C, 23.23; H, 1.12; N, 1.56. Infrared Spectrum (KCl): 1700 cm$^{-1}$ (carbonyl). Optical Rotation $[\alpha]_D^{25} = -14.97°$ (c 1.0, dimethylsulfoxide).

N-Methyl-4-{4-N-[(N-phthalimido)butyl]amino}phthalimide (7).

A mixture of 42 g (0.15 mol) of N-(4-bromobutyl) phthalimide (4) (Aldrich Chemical Co., Milwaukee, Wisconsin USA), 51.5 g (0.29 mol) of 4-amino-N-methylphthalmide (6) [Flitsch, Chem. Ber. 94:2494(1961)], and 300 ml of dimethylformamide was refluxed for one day. A yellow preciptate formed on cooling and was collected and dried to give 38.5 g of the bis-phthalimide (7). A sample was recrystallized from aqueous acetic acid to give fine yellow needles, m.p. 217°-218° C.

Analysis: Calculated for $C_{21}H_{19}N_3O_4$: C, 66.83; H, 5.07; N, 11.14. Found: C, 66.46; H, 4.99; N, 11.61.

N-Methyl-4-{6-N-[(N-phthalimido)hexyl]amino}phthalimide (8).

This compound was prepared in the same way as (7) from reaction of (6) and N-(6-bromohexyl)phthalimide (5). Recrystallization from aqueous acetic acid gave the bis-phthalimide (8) as fine yellow needles, m.p. 178°-179° C.

Analysis: Calculated for $C_{23}H_{23}N_3O_4$: C, 68.13; N, 5.72; N, 10.37. Found: C, 68.22; H, 5.82; N, 10.36.

4-{N-Ethyl-N-[4-(N-phthalimido)butyl]amino}-N-methylphthalimide (9).

A mixture of 38 g (0.1 mol) of the bis-phthalimide (7) and 100 ml of diethyl sulfate was heated at 160° C. for 45 minutes, then cooled to room temperature and poured into 3 liters of ice water. The yellow precipitate that formed was recrystallized from aqueous acetic acid to give 29 g of the N-ethylated derivative (9) as fine yellow needles, m.p. 164°-165° C.

Analysis: Calculated for $C_{23}H_{23}N_3O_4$: C, 68.13; H, 5.72; N, 10.37. Found: C, 68.01; H, 5.70; N, 10.56.

4-{N-Ethyl-N-[6-(N-phthalimido)hexyl]amino}-N-methylphthalimide (10).

This compound was prepared in the same way as (9) from reaction of (8) to give fine yellow needles from aqueous acetic acid, m.p. 135° C.

Analysis: Calculated for $C_{25}H_{27}N_3O_4$: C, 69.26; H, 6.28; N, 9.69. Found: C, 68.90; H, 6.04; N, 9.48.

6-[N-(4-Aminobutyl)-N-ethylamino]-2,3-dihydrophthalazine-1,4-dione (11).

A mixture of 29 g (0.072 mol) of the N-ethyl-bis-phthalimide (9), 80 ml of 95% hydrazine, and 300 ml of ethanol was refluxed for 2 hours. The reaction mixture was then cooled to room temperature and allowed to stand overnight. Evaporation under reduced pressure gave a pale yellow solid that was dried for 8 hours at 110° C. and reduced pressure of 0.1 mm Hg. The solid, amounting to 31.5 g, was stirred for 90 minutes in 150 ml of 10% hydrochloric acid and filtered. When the filtrate was neutralized with potassium hydroxide, a heavy precipitate occured which was filtered, dried, and recrystallized from aqueous dimethyl formamide to give 6.5 g of the amino-phthalazinedione (11) as a white powder, m.p. 255°-257° C.

Analysis: Calculated for $C_{14}H_{20}N_4O_2$: C, 60.85; H, 7.30; N, 20.28. Found: C, 60.67; H, 7.30; N, 20.18.

The efficiency of the amino-derivative (11) of the label in a chemiluminescent reaction and the detection limit of such derivative were determined as follows.

In determining efficiency, the label derivative and luminol (5-amino-2,3-dihydrophthalazine-1,4-dione) were oxidized individually at several levels in the picomolar range and related to the peak light intensities by a graph plot. Linear portions of the resulting curves allowed calculation of change in light intensity per unit concentration for the label derivative and for luminol. Efficiency of the label derivative was expressed as a percentage of the slope produced with luminol.

Reaction mixtures (150 μl) of the following composition were assembled in 6×50 mm test tubes mounted in a Dupont 760 Luminescence Biometer (E. I. duPont de Nemours and Co., Wilmington, Delaware U.S.A.) with a sensitivity setting of 820:50 mM sodium hydroxide, 0.07 μM hematin (Sigma Chemical Co., St. Louis, Missouri U.S.A.) and either the amino-derivative of the label or luminol at varying concentrations in the picomolar (pM) range (diluted with $H_2O$ from a 1 mM stock solution in 0.1 M sodium carbonate, pH 10.5). Each mixture was incubated 10 minutes at room temperature and 10 μl of 90 mM hydrogen peroxide was added to initiate the chemiluminescent reaction. Peak light intensity values were recorded from the instrument reading. All reactions were performed in triplicate and averaged. The efficiency of the label derivative (11) was found to be 84%.

Detection limit was defined as the concentration of the label derivative that produced a peak light intensity one and a half times the background chemiluminescence in the reaction mixture. The detection limit for the label derivative (11) was found to be 2 pM.

6-[N-(6-Aminohexyl)-N-ethylamino]-2,3-dihydrophthalazine-1,4-dione (12).

This compound was prepared from the N-ethyl-bisphthalimide (10) in the same manner as for (11). Recrystallization from water gave a 53% yield of aminophthalazinedione (12) as a white powder, m.p. 170° C.

Analysis: Calculated for $C_{16}H_{24}N_4O_2$: C, 63.13; H, 7.95; N, 18.41. Found: C, 62.82; H, 8.24; N, 18.74.

The efficiency of the amino-derivative (12) of the label and its detection limit were determined in the same manner as described above for the label derivative (11) except that the reaction mixture contained, in place of hematin, 0.27 μM microperoxidase (Sigma Chemical Co., St. Louis, Missouri U.S.A.) and also included 57.5 mM barbital buffer adjusted to pH 8.6; and the hydrogen peroxide reagent was made up in 10 mM Tris-HCl buffer [tris-(hydroxymethyl)aminomethane hydrochloride], pH 7.4. The efficiency was found to be 78% and the detection limit 2 pM.

6-{N-Ethyl-N-[4-(thyroxinylamido)butyl)]amino}-2,3-dihydrophthalazine-1,4-dione (13).

A mixture of 4.36 g (5 mmol) of N-trifluoroacetyl-thyroxine (2), 0.8 g (5 mmol) of carbonyldiimidazole, and 50 ml of tetrahydrofuran was refluxed for 10 minutes. The solvent was removed under vacuum to leave a solid residue of the imidazolide (3). This intermediate was not characterized but was immediately combined with a suspension of 1.38 g (5 mmol) of the amino derivative (11). After stirring for 2 days at room temperature, the solvent was removed under high vacuum and the solid residue washed with 80 ml of 10% hydrochloric acid.

The trifluroacetyl blocking group was removed by dissolving 2.07 g of the crude product in 35 ml of 0.5 M sodium hydroxide. After one hour at room temperature, the solution was neutralized to pH 5.0 with concentrated hydrochloric acid. A precipitate formed that was washed with $H_2O$ and dried. The dried solid was chromatographed on a column of 200 g of silica gel 60 (E. Merck, Darmstadt, West Germany) eluting with a 7:3 volume to volume (v:v) mixture of ethanol and 1 M triethylammonium bicarbonate, collecting 10 ml fractions. Fractions numbered 49 to 65 were combined and evaporated to give 680 mg of a cream-colored solid. This solid was taken up in 50 ml of 50% dimethylformamide and reprecipitated by the addition of $H_2O$. When dry, the solid amounted to 200 mg of the labeled conjugate (13) as a white powder, m.p. approximately 200° C. (decomposed).

Analysis: Calculated for $C_{29}H_{29}I_4N_5O_5$: C, 33.64; H, 2.82; I, 49.04; N, 6.77. Found: C, 34.02; H, 2.97; I, 48.55; N, 6.65.

6-{N-Ethyl-N-[6-(thyroxinylamido)hexyl]amino}-2,3-dihydrophthalazine-1,4-dione (14).

This compound was prepared from the amino-derivative (12) in the same manner as for (13) to give 200 mg of the labeled conjugate (14) as a white powder, m.p. approximately 200° C. (decomposed).

Analysis: Calculated for $C_{31}H_{33}I_4N_5O_5$: C, 35.02; H, 3.13; N, 6.59. Found: C, 33.37; H, 3.26; N, 6.10.

B. Binding Assay for Thyroxine

Five picomoles of the labeled conjugate (13) [the labeled conjugate (14) can be used as well] in 200 microliters (μl) of 0.1 N sodium hydroxide were applied to each of several small columns of Sephadex G-25 (Pharmacia Fine Chemicals, Uppsala, Sweden). The columns each had a bed volume of 1 ml and were prewashed with successive 4 ml volumes of 7% acetic acid (3 times), $H_2O$, and 0.1 M sodium hydroxide (3 times). One ml of 0.1 M sodium hydroxide was then applied to the top of each column and allowed to drain into the gel bed followed by application to each column of 200 μl of a solution containing various amounts of thyroxine standard in 10% serum (previously made thyroxine-free by charcoal treatment) and 90 mM sodium hydroxide. Each column was washed with 4 ml of 75 mM barbital buffer (pH 8.6) after which 300 μl of a preparation of antibody to thyroxine was added to each column. After a one hour incubation, the antibody-bound labeled conjugate was eluted from each column with a wash of 0.8 ml of the barbital buffer. An aliquot (95 μl) of each effluent was mixed with 55 μl of a 2 to 3.5 mixture (v:v) of 2 μM microperoxidase Sigma Chemical Co.; St. Louis, Missouri U.S.A.) in the barbital buffer and 0.2 M sodium hydroxide. After a ten minute incubation, 10 μl of 90 mM hydrogen peroxide was added to each mixture to initiate the chemiluminescent reaction. The light produced was measured in the Dupont 760 Biometer and recorded in peak light intensity units from the instrument reading. Each reaction was performed in triplicate and averaged.

The relationship of thyroxine concentration to peak light intensity is shown in Table 3 below.

TABLE 3

| thyroxine concentration (nM) | peak light intensity |
|---|---|
| 25 | 48.6 |
| 50 | 46.4 |
| 100 | 39.2 |
| 150 | 34.0 |
| 200 | 27.8 |

Twenty-eight serum samples containing unknown concentrations were obtained and assayed using the above-described chemiluminescent-labeled binding assay procedure (using the standard curve resulting from a plot of the Table 3 data) and using the commercially available TETRALUTE ® thyroxine radioassay kit (Ames Company Division, Miles Laboratories, Inc., Elkhart, Indiana 46515). The resulting correlation curve relating the chemiluminescent-assay values to the radioassay values had an equation of $y = 0.95x + 5.9$ nM with a correlation coefficient of 0.98 and a coefficient of variation of 13.1% for the chemiluminescent-assay.

These results demonstrate that the present labeled conjugates are useful in binding assays for ligands in liquid media.

What is claimed is:

1. In a chemiluminescent-labeled conjugate for use in specific binding assays of the general formula:

L(CO―)―(NH) labeling substance wherein L(CO―) is an antigenic protein or polypeptide bound to said labeling substance through an amide bond, characterized in that said —NH) labeling substance has the formula:

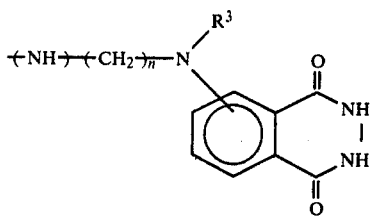

wherein $R^3$ is hydrogen or straight chain alkyl containing 1-4 carbon atoms and n=2-8.

2. The labeled conjugate of claim 1 wherein said antigenic protein or polypeptide has a molecular weight between 1,000 and 4,000,000.

3. The labeled conjugate of claim 1 wherein said antigenic protein or polypeptide is an antibody.

4. The labeled conjugate of claim 3 wherein said antibody is of the IgG class.

5. The labeled conjugate of claim 1 wherein said antigenic protein or polypeptide is insulin.

6. The labeled conjugate of claim 1 wherein said antigenic protein or polypeptide is thyroid stimulating hormone.

7. The labeled conjugate of claim 1 wherein said antigenic protein or polypeptide is a hepatitis-associated antigen.

8. The labeled conjugate of any one of claims 1-7 wherein said $-(NH)$ labeling substance has the formula:

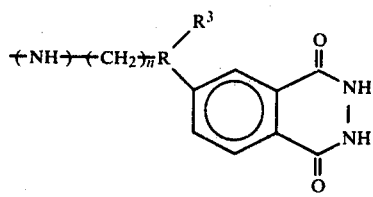

wherein $R^3$ is hydrogen or straight chain alkyl containing 1-4 carbon atoms and n=2-8.

9. The labeled conjugate of claim 8 wherein n=4 or 6.

10. The labeled conjugate of claim 9 wherein $R^3$ is ethyl.